US00PP28350P2

(12) United States Plant Patent
Lenard

(10) Patent No.: US PP28,350 P2
(45) Date of Patent: Aug. 29, 2017

(54) ***LEUCANTHEMUM* PLANT NAMED 'BL14007'**

(50) Latin Name: *Leucanthemum×superbum*
Varietal Denomination: BL14007

(71) Applicant: Birdie Lenard, Valley Center, CA (US)

(72) Inventor: Birdie Lenard, Valley Center, CA (US)

( * ) Notice: Subject to any disclaimer, the term of this patent is extended or adjusted under 35 U.S.C. 154(b) by 0 days.

(21) Appl. No.: 14/999,185

(22) Filed: Apr. 8, 2016

(51) Int. Cl.
*A01H 5/02* (2006.01)

(52) U.S. Cl.
USPC ..... Plt./285

(58) Field of Classification Search
USPC ..... Plt./285
See application file for complete search history.

*Primary Examiner* — Annette Para
(74) *Attorney, Agent, or Firm* — C. A. Whealy

(57) ABSTRACT

A new and distinct cultivar of *Leucanthemum* plant named 'BL14007', characterized by its compact, upright and mounded plant habit; freely branching habit; strong and upright flowering stems; freely flowering habit; re-flowering habit without vernalization; and large single inflorescences with yellow-colored ray florets.

1 Drawing Sheet

Botanical designation: *Leucanthemum×superbum.*
Cultivar denomination: 'BL14007'.

BACKGROUND OF THE INVENTION

The present invention relates to a new and distinct cultivar of *Leucanthemum* plant, botanically known as *Leucanthemum×superbum* and hereinafter referred to by the name 'BL14007'.

The new *Leucanthemum* plant is a product of a planned breeding program conducted by the Inventor in Valley Center, Calif. The new *Leucanthemum* plant is a naturally-occurring branch mutation of an unnamed proprietary selection of *Leucanthemum×superbum*, not patented. The new *Leucanthemum* plant was discovered and selected by the Inventor on a single flowering plant in a controlled environment in Valley Center, Calif. in 2012.

Asexual reproduction of the new *Leucanthemum* plant by terminal cuttings in a controlled greenhouse environment in Bonsall, Calif. since 2013 has shown that the unique features of this new *Leucanthemum* plant are stable and reproduced true to type in successive generations.

SUMMARY OF THE INVENTION

Plants of the new *Leucanthemum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BL14007'. These characteristics in combination distinguish 'BL14007' as a new and distinct *Leucanthemum* plant:

1. Compact, upright and mounded plant habit.
2. Freely branching habit.
3. Strong and upright flowering stems.
4. Freely flowering habit.
5. Re-flowering habit without vernalization.

6. Large single inflorescences with yellow-colored ray florets.

Plants of the new *Leucanthemum* differ primarily from plants of the parent selection in the following characteristics:

1. Plants of the new *Leucanthemum* are more compact than plants of the parent selection.
2. Plants of the new *Leucanthemum* have darker yellow-colored ray florets than plants of the parent selection.

Plants of the new *Leucanthemum* can be compared to plants of *Leucanthemum×superbum* 'Goldfinch', disclosed in U.S. Plant Pat. No. 24,499. In side-by-side comparisons, plants of the new *Leucanthemum* differ from plants of 'Goldfinch' in the following characteristics:

1. Plants of the new *Leucanthemum* are more compact than plants of 'Goldfinch'.
2. Plants of the new *Leucanthemum* do not require a vernalization treatment for re-flowering and abundant flowering whereas plants of 'Goldfinch' require a vernalization treatment for re-flowering and abundant flowering.
3. Inflorescences of plants of the new *Leucanthemum* had darker yellow-colored ray florets than plants of 'Goldfinch'.

Plants of the new *Leucanthemum* can be compared to plants of *Leucanthemum×superbum* 'Real Dream', disclosed in U.S. Plant Pat. No. 25,664. In side-by-side comparisons, plants of the new *Leucanthemum* differ from plants of 'Real Dream' in the following characteristics:

1. Plants of the new *Leucanthemum* are more compact than plants of 'Real Dream'.
2. Plants of the new *Leucanthemum* do not require a vernalization treatment for re-flowering and abundant flowering whereas plants of 'Real Dream' require a vernalization treatment for re-flowering and abundant flowering.
3. Inflorescences of plants of the new *Leucanthemum* had darker yellow-colored ray florets than plants of 'Real Dream'.

BRIEF DESCRIPTION OF THE PHOTOGRAPHS

The accompanying colored photographs illustrate the overall appearance of the new *Leucanthemum* plant showing the colors as true as it is reasonably possible to obtain in colored reproductions of this type. Colors in the photographs may differ slightly from the color values cited in the detailed botanical description which accurately describe the colors of the new *Leucanthemum* plant.

The photograph at the bottom of the sheet comprises a side perspective view of a typical flowering plant of 'BL14007' grown in a container.

The photograph at the top of the sheet comprises a close-up view of a typical flowering plant of 'BL14007'.

DETAILED BOTANICAL DESCRIPTION

The aforementioned photographs and following observations and measurements describe plants grown in 10-cm containers during the summer in an outdoor nursery in Bonsall, Calif. and under cultural practices typical of commercial *Leucanthemum* production. During the production of the plants, day temperatures ranged from 25° to 31° C., night temperatures ranged from 14° C. to 20° C. and light levels ranged from 10,000 to 12,500 foot-candles. Plants were six weeks from planting when the photographs and the description were taken. In the following description, color references are made to The Royal Horticultural Society Colour Chart, 2007 Edition, except where general terms of ordinary dictionary significance are used.

Botanical classification: *Leucanthemum×superbum* 'BL14007'.

Parentage: Naturally-occurring branch mutation of an unnamed proprietary selection of *Leucanthemum×superbum*, not patented.

Propagation:

*Type*.—Terminal vegetative cuttings.

*Time to initiate roots, summer*.—About two weeks at temperatures about 21° C. to 24° C.

*Time to initiate roots, winter*.—About three weeks at temperatures about 16° C. to 18° C.

*Time to produce a rooted young plant, summer*.—About four to five weeks at temperatures about 21° C. to 24° C.

*Time to produce a rooted young plant, winter*.—About 35 to 40 days at temperatures about 16° C. to 18° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching, medium density.

Plant description:

*Plant and growth habit*.—Herbaceous perennial; compact, upright and mounded plant habit; moderately vigorous to vigorous growth habit; freely branching habit with about twelve basal branches developing per plant.

*Plant height*.—About 22 cm.

*Plant width*.—About 26 cm.

*Basal branch description*.—Aspect: Upright. Strength: Strong. Length: About 19 cm. Diameter: About 5 mm. Internode length: About 1.8 cm. Texture: Sparsely pubescent. Color: Close to 137B.

*Leaf description*.—Arrangement: Alternate; simple; sessile. Length: About 9.5 cm. Width: About 2.1 cm. Shape: Narrowly spatulate. Apex: Acute. Base: Attenuate; clasping. Margin: Dentate to serrate. Texture and luster, upper surface: Smooth, glabrous; slightly shiny. Texture and luster, lower surface: Mostly glabrous; margins, sparsely pubescent; slightly shiny. Venation pattern: Prominent midvein and arcuate lateral veins. Color: Developing leaves, upper and lower surfaces: Close to 137C. Fully developed leaves, upper surface: Close to N137B; venation, close to 147B. Fully developed leaves, lower surface: Close to 147B; venation, close to 147C.

Inflorescence description:

*Appearance*.—Single inflorescence form with recurving ray florets and tubular disc florets on a flat disc; inflorescences held upright on strong peduncles, inflorescences race upright to slightly outwardly; ray and disc florets develop acropetally on a capitulum.

*Fragrance*.—Faint, slightly sour.

*Flowering response*.—Plants do not require a vernalization treatment for re-flowering and abundant flowering; long flowering period, plants flower naturally from early to mid- summer in Southern California.

*Postproduction longevity*.—Inflorescences maintain good substance for about eight to ten days on the plant; inflorescences persistent.

*Quantity of inflorescences*.—Freely flowering habit, about 20 inflorescences develop per plant.

*Inflorescence size*.—Diameter: About 6.5 cm to 7 cm. Depth (height): About 1.8 cm. Disc diameter: About 2.5 cm.

*Receptacles*.—Height: About 8 mm. Diameter: About 3 cm. Color: Close to 137B.

*Inflorescence buds*.—Height: About 1.6 cm. Diameter: About 2 cm. Shape: Flattened sphere. Color: Close to 1B.

*Ray florets*.—Quantity per inflorescence: About 54 arranged in about three whorls. Length: About 2.7 cm. Width: About 8 mm. Shape: Spatulate. Apex: Tri-dentate. Base: Attenuate. Margin: Entire. Aspect: Horizontal to recurved. Texture, upper and lower surfaces: Smooth, glabrous; velvety; longitudinally ridged. Color: When opening, upper surface: Close to 4B. When opening, lower surface: Close to 4C to 4D. Fully opened, upper surface: Close to 4D; towards the apex, close to 4C; color becoming closer to 8D with development. Fully opened, lower surface: Close to 4D; color becoming closer to 8D with development.

*Disc florets*.—Quantity per inflorescence: About 450 massed at the center of the receptacle. Length: About 7 mm. Diameter: About 2.5 mm. Shape: Short, fused tubular. Apex: Acute, five-pointed. Texture, inner and outer surfaces: Smooth, glabrous. Color, when opening: Apex: Close to 17A. Mid-section and base: Close to 1C. Color, fully opened: Apex: Close to 16A. Mid-section and base: Close to 1C.

*Involucral bracts*.—Quantity per inflorescence: About 60 arranged in about three to four whorls. Length: About 8 mm. Width: About 2.5 mm. Shape: Lanceolate. Apex: Acute. Base: Truncate. Margin: Entire, membraneous. Texture and luster, upper surface: Smooth, glabrous; glossy. Texture and luster, lower surface: Smooth, glabrous; matte. Color, upper surface: Close to 137C. Color, lower surface: Close to 147B.

*Peduncles*.—Length: About 4.4 cm. Diameter: About 3 mm. Strength: Strong. Aspect: Upright. Texture: Scattered pubescence; longitudinally ridged. Color: Close to 147B.

*Reproductive organs*.—Androecium: Present on disc florets only. Quantity per floret: Five per disc floret. Filament length: About 1.5 mm. Filament color: Close to 157D. Anther shape: Oblong. Anther length: About 2 mm. Anther color: Close to 15A. Pollen amount: Moderate. Pollen color: Close to 17A. Gynoecium: Present on ray and disc florets. Quantity per floret: One. Pistil length: About 5 mm. Stigma shape: Bi-parted. Stigma color: Close to 3B. Style length: About 2 mm. Style color: Close to 145D. Ovary color: Close to 147D.

*Seeds and fruits*.—Seed and fruit production have not been observed on plants of the new *Leucanthemum*.

Disease & pest resistance: Plants of the new *Leucanthemum* have not been observed to be resistant to pathogens and pests common to *Leucanthemum* plants.

Garden performance: Plants of the new *Leucanthemum* have been observed to have good garden performance and to tolerate wind and rain, to be suitable for USDA Hardiness Zone 5b to 9b.

It is claimed:

1. A new and distinct *Leucanthemum* plant named 'BL14007' as illustrated and described.

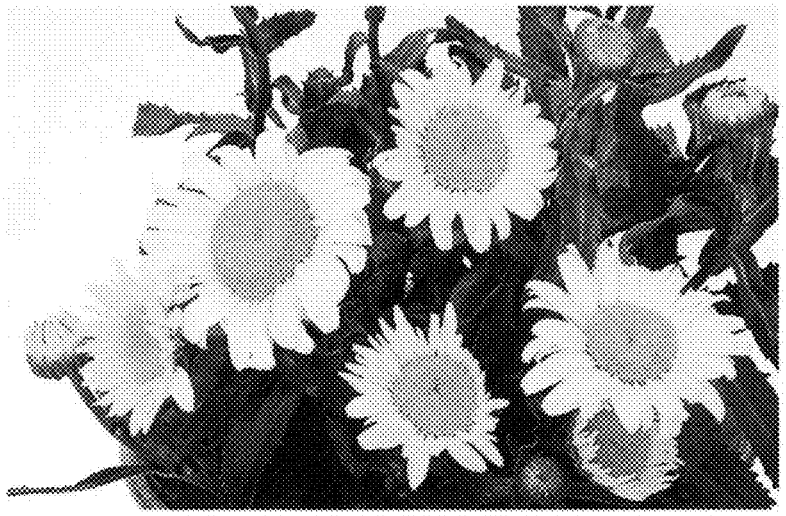
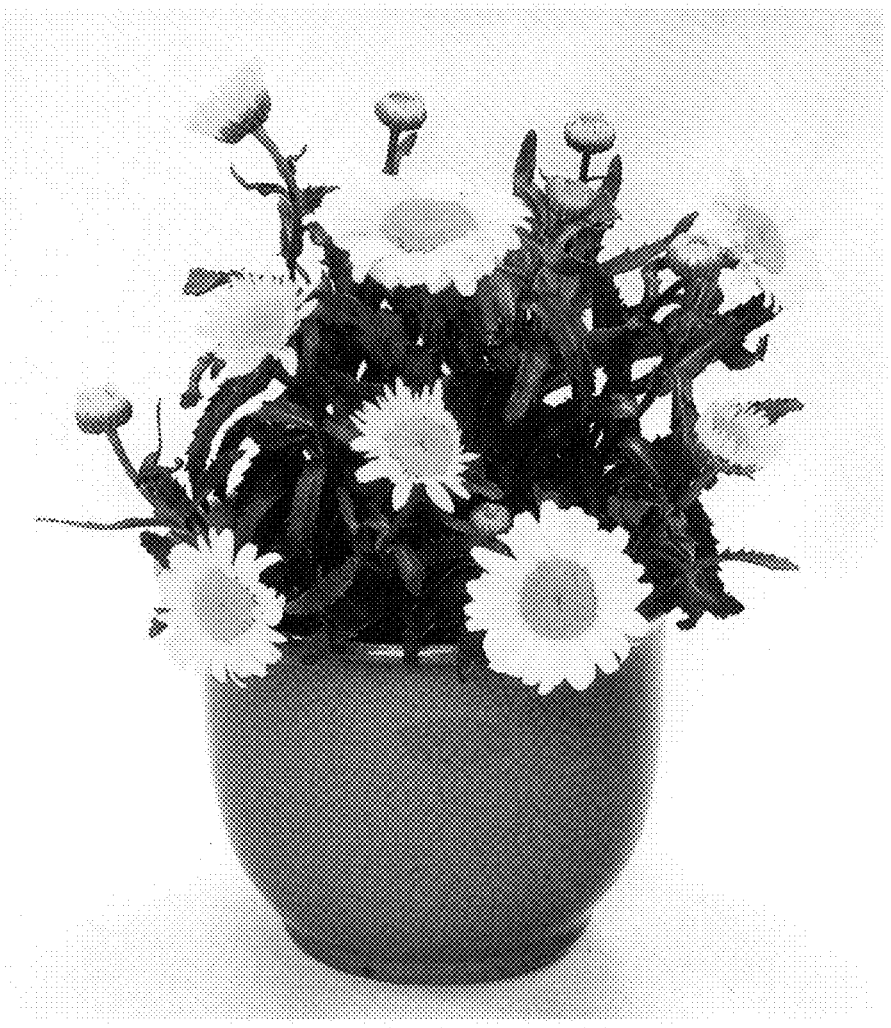

* * * * *